United States Patent [19]

Atkinson

[11] Patent Number: 4,635,621

[45] Date of Patent: Jan. 13, 1987

[54] LAVAGE SYSTEM WITH REPLACEABLE PUMP

[75] Inventor: Robert W. Atkinson, Dover, Ohio

[73] Assignee: Snyder Laboratories, Inc., Dover, Ohio

[21] Appl. No.: 445,806

[22] Filed: Dec. 1, 1982

[51] Int. Cl.⁴ .............................................. A61H 7/00
[52] U.S. Cl. .................................. 128/66; 239/102.1
[58] Field of Search .................. 128/66; 417/360, 326; 239/102; 604/30, 150; 433/229

[56] References Cited

U.S. PATENT DOCUMENTS

| | | | |
|---|---|---|---|
| 3,597,118 | 8/1971 | Kolfertz | 417/360 |
| 3,731,676 | 5/1973 | Rebold | 128/66 |
| 3,835,846 | 9/1974 | Kurtz | 128/66 |
| 3,912,168 | 10/1975 | Mullins et al. | 239/102 |
| 3,960,466 | 6/1976 | Taylor | 128/66 |
| 4,108,167 | 8/1978 | Hickman et al. | 128/66 |
| 4,178,931 | 12/1979 | Lind et al. | 128/66 |
| 4,303,376 | 12/1981 | Siekmann | 417/360 |

Primary Examiner—Robert Peshock
Assistant Examiner—J. Hakomaki
Attorney, Agent, or Firm—Paul David Schoenle

[57] ABSTRACT

A lavage system including a motor having a drive member, a pump housing having a door, a pump having a pump body and a driven member, a means for coupling the motor drive member and the pump driven member, and a means activated by the closing of the housing door for gripping the pump body and securing it within the pump housing. The gripping and securing means includes a pair of fingers which pass through a portion of the pump body, and a wedge on the door which forces the fingers apart and against the pump body when the door is closed. The means for coupling the drive member and the driven member and the gripping and securing means are engageable by the pump along the same direction for ease of insertion of the pump in the housing.

7 Claims, 6 Drawing Figures

LAVAGE SYSTEM WITH REPLACEABLE PUMP

BACKGROUND OF THE INVENTION

1. Field of the Invention

The invention in general relates to the field of medical, dental and therapeutic lavage, and more particularly to a mechanized lavage system in which the pump assembly is replaceable, permitting the use of disposable and/or sterilizable pumps.

2. Description of the Prior Art

Lavage, or the washing of tissue, is perhaps as old as medicine itself. In the early years it consisted of the application of fluid, generally a liquid such as water, to tissue to wash away dirt or debris. In more modern times, it has become more important, and more thorough, due to an awareness of bacteria and other organisms that may cause infection. In the last several decades, mechanized lavage systems have become common.

Before proceeding to the discussion of prior art mechanized devices it will be useful to clarify terminology. The word "lavage" is used ambiguously in the literature, sometimes referring to a pulsating stream type washing or therapy, sometimes referring to a stream type of washing, and sometimes also including an aspiration function. In this document, unless the context clearly indicates otherwise, "irrigation" shall mean the stream type of washing "pulsatile lavage" shall mean the pulsating type of washing or therapy, and the word "lavage" shall mean the broadest sense of the term, referring to any one of, or combinations of, irrigation, pulsatile lavage, and aspiration.

Medical, dental and therapeutic lavage systems are often used in situations requiring sterility or at least a high degree of cleanliness. For use in such situations all parts of the system which contact the lavage fluid should be sterilizable and/or easily replaceable. Optimally, these parts of the system should be disposable, since this permits replacement with sterilized parts after each use. Since the pump in a lavage system necessarily must contact the lavage fluid it is important that the replaceable parts include the pump.

U.S. Pat. No. 3,912,168 issued to Keith M. Mullins, et al., and No. 3,993,054 issued to Gordon Arthur Newman disclose lavage systems in which all portions which contact the lavage fluid are sterilizable and/or replaceable. Both these systems use a peristaltic pump, consisting of a tube impacted by a cam. In these systems, because the peristaltic tube is flexible the parts that contain the tube actually form the pumping chamber walls, and are subject to considerable stress. It has been found that these walls, especially the front door portion can yield during use with result that pump partsmay be sent flying through an operating room during surgery. A pump in which all parts which bear the direct force of the pumping action are enclosed within a housing, and at the same time the pump parts that contact the fluid are easily replaceable and/or disposable, would be highly desirable.

SUMMARY OF THE INVENTION

It is an object of this invention to provide a lavage system in which the parts which contact the lavage fluid are all sterilizable and/or replaceable and which overcomes the disadvantages of the prior art systems.

It is another object of the invention to provide a lavage system in which the pump parts that contact the lavage fluid are disposable.

It is a further object of the invention to provide a lavage system that provides one or more of the above objects and in which the parts may be replaced quickly with a minimum of skill.

The invention comprises a medical, dental or therapeutic lavage apparatus comprising a motor having a drive member, a pump housing including a door, a pump including a pump body and a driven member, the pump body comprising a pump chamber, a means for coupling the motor drive member with the pump driven member, and means activated by the closing of the door for gripping the pump body and securing it within the pump housing. Preferably the means for gripping and securing comprises a means for loosely supporting the pump body within the housing when the door is open and for gripping the pump body and holding it securely within the housing when the door is closed. Preferably the means for gripping includes a pair of gripping members, at least one of which is moveable relative to the other member, and a means for forcing the gripping members to engage at least a portion of the pump body in opposing directions. Preferably the pump body includes at least one flange and the means for gripping includes a means for gripping the flange. In the preferred embodiment there are two pairs of flanges, the pairs located on opposing sides of the pump body, and two pairs of gripping members, each pair fitting between a pair of flanges, and the means for forcing comprises a wedge mounted on the door for forcing the gripping members apart and into contact with the flanges when the door is closed.

In another aspect of the invention a medical, dental, or therapeutic lavage apparatus is provided which comprises a motor having a drive member, a pump housing, a reciprocating pump having a pump body and a reciprocating driven member, a means for coupling the drive member and the driven member for movement in unison along the reciprocation direction, the means for coupling engageable by motion of the pump body along a first direction, a means engageable by the pump body along the first direction for supporting the pump body within the housing, and a means activated by the closing of the door for locking the pump body to the support means.

It has been found that the invention not only prevents the parts from flying around operating rooms, but also increases the reliability and longevity of the system by preventing unnecessary vibration of the moving parts and at the same time significantly reduces the noise of the system. Surprisingly it has also been found that the disposable parts may be replaced much more quickly than in the prior art systems, apparently because proper alignment of the parts is more certain with the system, and any inexact alignment that may occur can be tolerated by the system without leading to rapid destruction of the moving parts.

Numerous other features, objects and advantages of the invention will now become apparent from the following detailed description when read in conjunction with the accompanying drawings, in which:

DESCRIPTION OF THE PREFERRED EMBODIMENT

Figure 1:
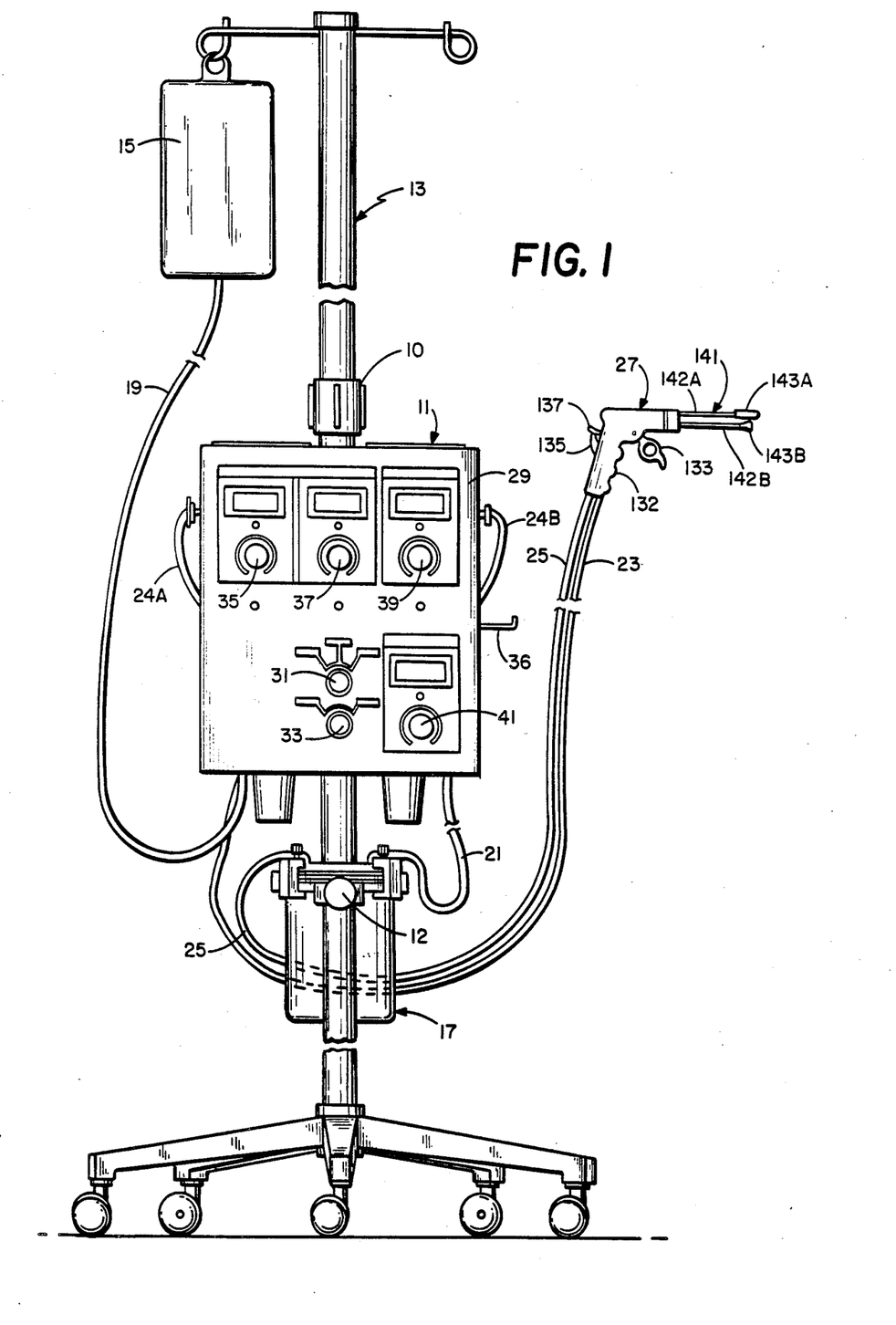
FIG. 1 is an external front view of a lavage system in accordance with a preferred embodiment of the invention.
Figures 2, 3:
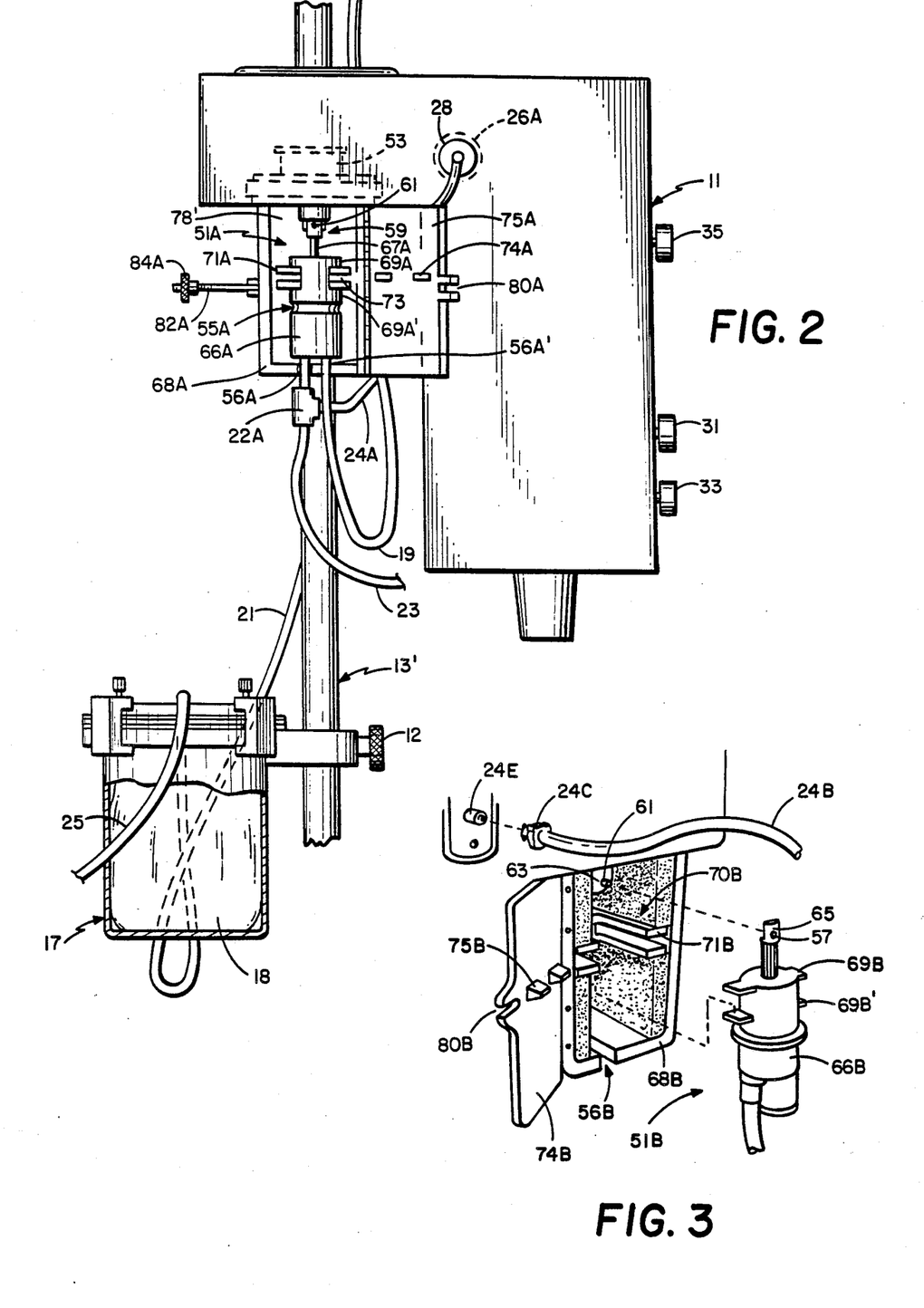
FIG. 2 is a side view of the housing of the system of FIG. 1 showing the preferred pulsatile lavage/irrigation pump.
FIG. 3 is a side view of the housing showing the suction pumping chamber, and indicating the manner of insertion of the pump.

Referring to FIGS. 1-3, the preferred embodiment of the lavage system according to this invention is shown. The system includes a housing 11 mounted on a movable stand 13 along with a supply 15 of fluid such as saline solution. Below the housing 11 and also mounted to the stand 13 is a drainage tank 17. The fluid supply 15 is connected to a pulsatile lavage/irrigation pump 51A (shown in FIG. 2) in the housing 11 by line 19, and the drainage tank 17 is likewise connected to a suction pump 51B (shown in FIG. 3) in the housing 11 by line 21. A pulsatile lavage/irrigation fluid line 23 connects the pump 51A to a lavage handpiece 27 to provide a stream of fluid at nozzle 143B. A suction line 25 connects the lavage handpiece 27 to the drainage tank 17. The vacuum line 21, connecting the drainage tank 17 to the suction pump 51B in the housing 11, provides fluid suction at the nozzle 143A via line 25. All the parts of the system that contact the lavage fluid, including the fluid supply bag 15, lines 19, 24A, 24B, 21, 23, and 25, drainage bag 18, couplings 24C and 24D, filter 28, T's 22A and 22B, lavage handpiece 27, and pumps 51A and 51B, are replaceable, sterilizeable and disposable.

The housing 11 contains circuitry, motors and pumps which provide pulsatile lavage and irrigation functions by pumping fluid from the supply 15 to the lavage head 27 via line 23 and provide an aspirating function by pumping fluid from the lavage head 27 via line 25 to the drainage tank 17 by providing vacuum at line 21. Hereinafter in this description, for simplicity and to avoid suggesting that there may be more than two motors and pumps, we shall refer to the motor, pump, and the associated components which provide both the pulsatile lavage and irrigation functions by the designation PL/IR.

Referring to FIG. 1, the pulsatile lavage, irrigation and suction functions are controlled at control board 29. A pair of switches 31, 33 operate the PL/IR and suction pumps, respectively. The suction control switch 33 is a two-position on/off switch, while the PL/IR control switch 31 is a three-position switch having an "off" position, a "lavage" (here short for pulsatile lavage) position and an "irrigation" position. The PL/IR control switch 31 is used to switch the PL/IR motor from "off" to "lavage" and "irrigation" control modes with "lavage" mode control being effected by control knobs 35 and 37 and "irrigation" mode control being effected by knob 39. In this embodiment the suction pump is operable in only a single "suction" mode which is controlled by knob 41.

It can be seen that the system can be controlled in three "on" modes: "lavage," "irrigation," and "suction." Further, "lavage" when used in connection with knob 31 is short for the term pulsatile lavage used elsewhere herein. Moreover, both the "lavage" and "irrigation" modes provide irrigation in the sense that they both provide a stream of liquid. Likewise, while in the present embodiment the "lavage" mode does not control suction, suction is generally considered to be an integral part of surgical lavage. For this reason, the choice of terminology chosen to distinguish the three functions of the preferred system should not be considered to be limiting when these terms are used in somewhat different senses in other contexts.

Having provided a brief orientation to the drawings and the functions of the preferred system we shall now return to FIGS. 1 thru 3 and proceed with a more detailed description.

Stand 13 includes a collar 10 for adjusting the height of the upper portion, and thus the height of fluid supply, above the housing 11. Drainage tank 17 also includes a knobbed set screw 12 for adjustment of its height.

We have already described the connection of tubes 19, 21, 23, and 25. The system also includes tubes 24A and 24B. One end of line 24A connects to "T" 22A in line 23 and the other end connects to the pressure transducer coupling 24D. The connection is made by means of a leur lock connector 24F having a filter 28 attached to prevent contamination of the fluid in tube 23 by transducer 26A (FIG. 2). One end of line 24B connects to "T" 22B (not shown) in line 21 and the other end connects to suction transducer coupling 24E via leur lock connector 24C. The transducers 26A and 26B will be discussed in more detail in connection with FIG. 6. Also shown in FIG. 2 is a disposable drainage bag 18 which optionally fits within tank 17. In an alternative embodiment bag 18 may be replaced by a disposable rigid cannister.

Referring to FIG. 1, the lavage handpiece 27 in the preferred embodiment includes a pistol-shaped body 132 and a pair of pinch valves 133 and 135, which are secured in hollows molded in body 132. A pair of cylindrical channels are formed within body 132 of an appropriate size to accept the ends of tubing 23 and 25. Pinch valve 133 is rotatable about pin 136 to pinch off tubing 23. Serrated arm 137 holds pinch valve 135 in an open or closed position. It is made of a flexible material so that it may be raised upward to release pinch valve 135 as desired. Attached to the lavage handpiece 27 is a nozzle tube assembly 141 which comprises two semi-rigid tubes 142A and 142B held in a plug 140, and a pair of nozzles 143A and 143B attached to the ends of tubes 142A and 142B respectively. The proximal ends of tubes 142A and 142B fit into the open ends 139 of tubes 23 and 25 within body 132. In the preferred embodiment these nozzles and tubes form a replaceable assembly. The particular form of the nozzle is described in detail in a companion application, and since this particular form is not a part of the present invention it will not be discussed further herein.

Referring to FIGS. 2-5, the pulsatile lavage/irrigation pump 51A and suction pump 51B are shown. Each pump 51A and 51B is attached to an electric driving motor, which in the preferred embodiment is a linear reciprocating motor; however, only one motor 53 is shown (attached to pump 51B) as the other motor is identical. Each motor, such as 53, is connected to its pump, such as 51B, by a coupling 59. Each coupling 59 consists of a pin 61 and a pair of flange sections 63, 65 associated with the motors 53 and pumps (51A or 51B) respectively. Each pin 61 is located on the motor flange 63 and inserts into a hole 57 in the pump flange 65. Each flange 65 is connected to a driven member or piston rod, piston rod 67A in the case of pump 51A and piston rod 67B in the case of pump 51B.

Figures 4, 5:
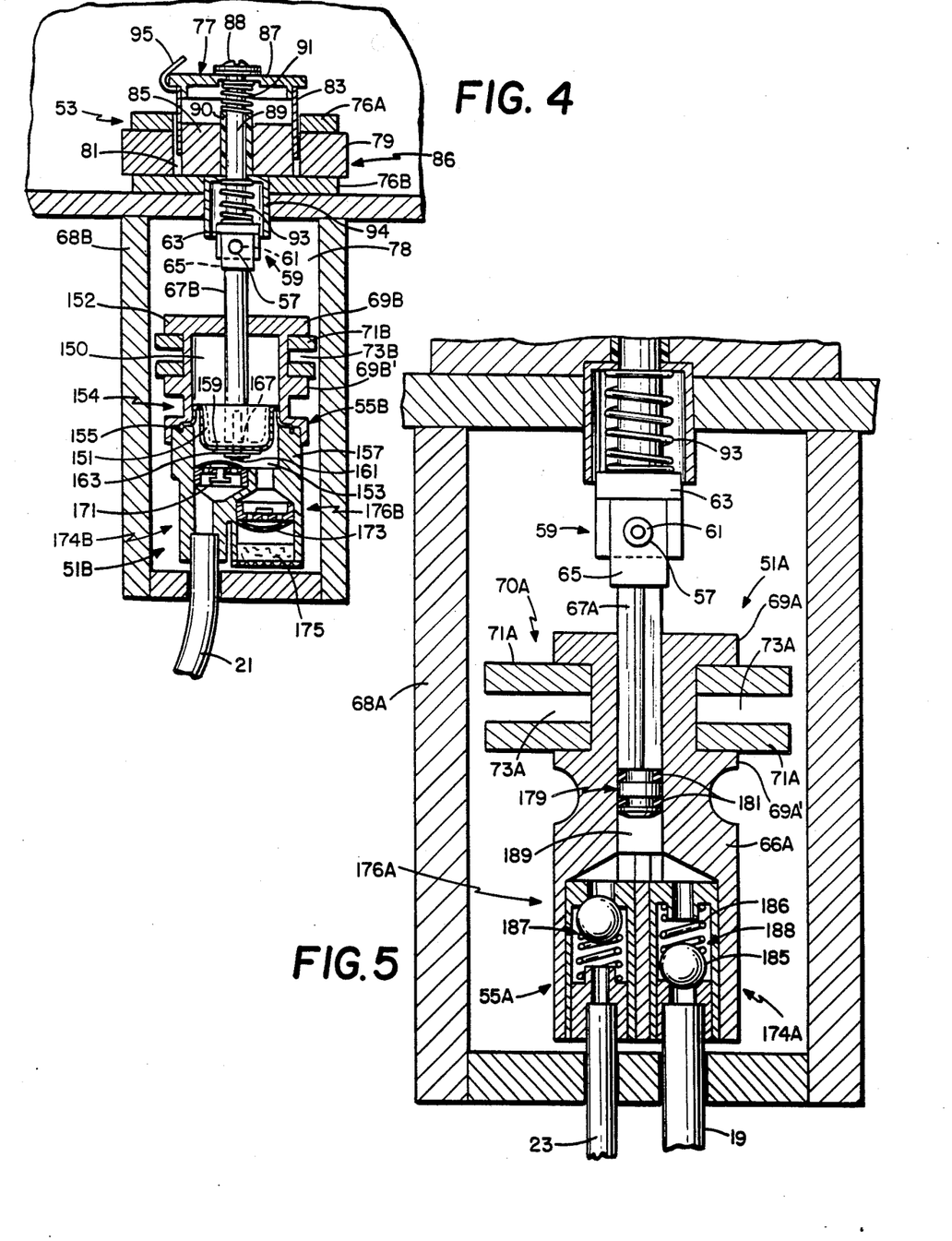
FIG. 4 is a (cut-away) sectional view of the preferred suction pump housing, pump, and an embodiment of a motor according to the invention.
FIG. 5 is a (cut-away) sectional view of the preferred pulsatile lavage/irrigation pump housing and pump used in the invention.

Referring to FIG. 4, and in particular, the lower portion of the figure, the suction pump 51B is shown. The pump includes a pump body 55B having a upper portion 152 and a lower portion 157 which enclose a cylindrical chamber 154, which chamber is divided into a upper portion 150 and a lower portion 153 by a diaphragm 151 In this document "pump chamber" generally refers to that portion of the pump that contains and directs the force exerted by the driven member so as to produce a flow of fluid. The "pump body" may be the same as the pump chamber in some embodiments, but in the one disclosed herein it includes flanges such as 69B and valves such as 173. Diaphragm 151 includes an outer lip 155 which is secured between the two housing portions 152 and 157. The center part of diaphragm 151 is sandwiched between a cup 159 and washer 163 and the assembly is secured to rod 67B by a screw 161 which screws into a threaded hole 167 in the end of rod 67B. Inlet umbrella valve 171 and outlet umbrella valve 173 seat in inlet and outlet passageways to chamber 153. Filter 175 seats in the lower portion of the outlet passageway.

Referring to FIG. 5, the PL/IR pump 51A is built somewhat differently than the suction pump because of its different function The molded pump body 66A encloses a cylindrical chamber 189 which is sealed by plunger 179, which is comprised of two O-rings 181 which fit into grooves in the end of rod 67A. The outlet and inlet valves 187 and 188 respectively are ball valves comprised of resilient balls such as 185 which are normally held in the closed position by springs 186.

Referring to FIG. 3, the apparatus for holding a pump within the housing 11 shall be described in reference to the suction pump 51B. An upper pair of flanges 69B and a lower pair of flanges 69B' extend from the pump body 66B. Within suction pump housing 68B is a suction pump support 70B which is shaped somewhat like a four-fingered tuning fork having fingers 71B. Pump 51B fits into housing 68B with flanges 69 passing above the upper pair of fingers 71B and flanges 69B passing below the lower pair of fingers 71B. A backing plate 78 (not shown in FIG. 3) is located so that pump 51B slides up against it when pin 61 has fully entered the hole 57 in flange 65 and flange 65 and 63 engage. Door 74B mounted on enclosure 68B may then be closed. When door 74B is closed, wedges 75B located on door 74B slip in between the fingers 71B forcing them apart and causing them to firmly engage flanges 69B and 69B' on pump 51B, thus holding pump 51B firmly in place. Rod 82B is then pivoted into slot 80B in door 74B and locking nut 84B is screwed inward to secure the door (this is perhaps best seen in FIG. 2). Referring to FIG. 5, pump 51A is likewise secured in housing 68A by slipping flanges 69A and 69A' about fingers 71A and, closing door 75A so that wedges 74A force fingers 71A open, slipping rod 82A into slot 80A and screwing nut 84A tight to secure the door.

Referring to FIG. 4, the motor 53, as stated above, is a linear reciprocating motor. It comprises a coil 83 and a core 86. Coil 83 is fixed to reciprocating section 77 which is the drive member of motor 53. Core 86 comprises an outer permanent magnet portion 79 and an inner non-magnetized but magnetically permeable portion 85. A cylindrical slot 81 is formed within core 86, and coil 83 moves within this slot. Magnetically permeable steel plates 76A and 76B sandwich the permanent magnet, and also may be considered as part of the motor core. Coil 83 is mounted on plate 87, and plate 87 is in turn attached to drive shaft 89 by screw 88. A hollow cylindrical bearing 90 fits into a cylindrical bore in core 86 and shaft 89 slides within bearing 90. Helical coil spring 91 is located on shaft 89 with the axis of the spring corresponding to the axis of the shaft, and with one end of the spring seating against plate 87 and the other end of the spring seated against bushing 90. Similarly the coil spring 93 fits coaxially about the bottom of the shaft 89 and seats between the top of flange 63 and a spring enclosure 94 which forms an integral part of bushing 90. It is noted that the springs 91 and 93 will function properly as long as one end is seated against a portion of the motor that is moveable with the coil while the other end is seated against a portion of the motor which is fixed to the core. Thus, in the context of providing a seat for the spring, bushing 90 may in this embodiment be considered to be part of the motor core. Coil 83 is electrically connected to circuitry in the housing by means of braided wires 95.

Figure 6:
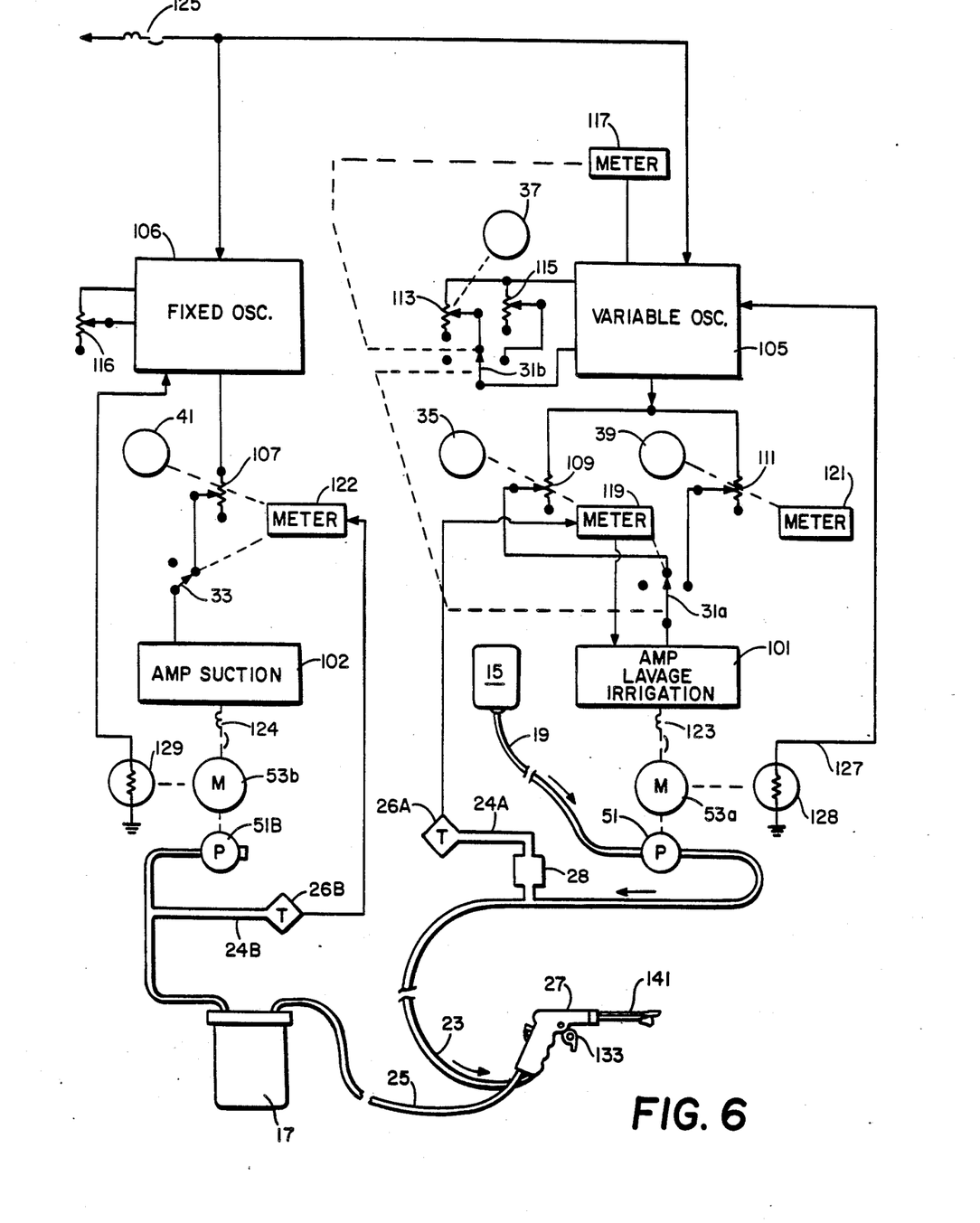
FIG. 6 is a block diagram showing the operation of the controls and various functions of the preferred embodiment of the invention.

Referring to FIG. 6, a discussion of the electrical circuitry in terms of a functional diagram is shown. In FIG. 6 the physical connection between pump 51A and motor 53a and pump 51B and motor 53b is shown by a dotted line. Power for the motors 53a and 53b are supplied by a signal provided by amps 101 and 102 respectively which is supplied to the motors through circuit breakers 123 and 124 respectively. Oscillating signals which are amplified by amplifiers 101 and 102 are provided by oscillators 105 and 106 respectively. Power to the oscillators is provided through circuit breaker 125.

The switches in FIG. 6 correspond to the switches in FIG. 1. These switches are actually double pole switches. The two poles of switch 31 are shown separately at 31a and 31b in FIG. 6 for clarity. The dotted line indicates that the two switches move together.

As can be seen in FIG. 6, switch 33 has a closed position in which it connects the fixed oscillator 106 to the suction amplifier 102, which is the suction "on" position, and an open circuit position which is the suction "off" position. In the "on" position switch 33 also activates meter 122 to read the vacuum from the suction transducer 26B. This is shown by the dotted line. Meter 122 could also be connected to read the power going through variable resistor 107, or the power off the amplifier 102, both of which would give a meaningful output to the meter.

The far left position of switches 31a and 31b is an open circuit "off" position. In the central position switch 31a connects variable resistor 109 which is controlled by knob 35 into the circuit between oscillator 105 and amp 101. Variable resistor 109 controls the amplitude of the signal to amplifier 101 and thus controls the power output of the amplifier and ultimately of the pump. Since the power output of the pump is directly related to either the rate of flow or the pressure, meter 119 can be calibrated in either percent of power units, pressure units, or rate of flow units. In the embodiment described, it is chosen to calibrate the meter in pressure units, and the pressure is read off pressure transducer 26A by meter 119 when switch 31a is in the central position. The pressure units chosen are pounds per square inch. Of course, any other pressure units, such as millimeters of mercury could also be chosen. In the central position, switch 31b connects variable resistance 113 into the variable oscillator 105 circuitry. Variable resistance 113 is controlled by knob 37, the pulsatile lavage frequency control, to control the frequency of variable oscillator 105. In the central position switch 31b also connects meter 117 to the circuitry of variable oscillator 105. In this position of switch 31b, meter 117 displays the frequency of oscillation of the variable oscillator 105. In the far right position switch 31a connects variable resistance 111 between oscillator 105 and amplifier 101. Variable resistance 111 is controlled by knob 39 which is the irrigation power control. Meter 121 displays the output of variable resistance 111. Again this output can be calibrated in either pressure units, rate of flow units, or a power unit. In the present embodiment it is chosen to calibrate it in percent of flow. In the far right position, switch 31b connects variable resistor 115 into the electrical circuit of variable oscillator 105. Variable resistance 115 is not controlled by an external knob, but rather is controlled by a "behind the set" control which determines the "fixed" frequency of the irrigation mode. Generally this resistance is set so that a high oscillation frequency, i.e. in the range between 30 and 40 cycles per second is chosen since a high frequency provides a nearly continuous flow. In the embodiment shown switch 31b when switched to the far right position deactivates the meter 117, although one obviously could choose to leave the meter connected in this situation if one desired to read out the "fixed" frequency.

The oscillation frequency of fixed oscillator 106 is determined by variable resistance 116, which is also a "behind the set" control. The setting of variable resistance 116 determines the frequency of the suction motor and pump.

Also shown in FIG. 6 are thermistors 128 and 129 which are physically attached to motors 53a and 53b as shown by the dotted lines. Thermistors 128 and 129 are temperature sensitive resistors which in a voltage divider circuit will vary the voltage output of the circuit proportionally to the temperature of the motor. As the temperature of the motor increases the internal resistance of the moving coil increases which reduces the effective power produced by the motor. The output of the voltage divider circuit incorporating thermistors 128 and 129 is fed into the circuitry of the oscillators 105 and 106 respectively. The circuitry is arranged so that this output causes the power input to the oscillators 105 and 106 respectively, and therefore the power level of the oscillator output signal to increase precisely as needed to account for the variation of performance of motors 53a and 53b respectively with temperature.

FIG. 6 also shows a connection between pressure transducer 26A and amplifier 101 thru meter 119. By means of this connection, the circuitry causes the amplifier 101 to shut down if the pressure in line 23 rises above a certain predetermined pressure, and to turn back on when the pressure drops below that predetermined pressure. This circuitry causes motor 53a and pump 51A to shut down whenever valve 133 on the lavage handpiece (FIG. 1) is closed, and to resume operation when the valve 133 is opened.

The various electronic parts in the functional diagram 6 are well understood in the electrical art and one skilled in the electrical art can generally build such parts once their function has been described. They play only a supporting role in the present application and shall not be described further herein.

The materials from which the various parts of the invention are made are for the most part evident from the functions; we shall briefly review the preferred materials, although it should be understood that many other suitable materials could be used. The PL/IR fluid supply container 15 is formulated out of vinyl plastic as are the various fluid tubes such as 19, 21, 23, and 25. Handpiece 27 is molded out of ABS plastic, and drainage tank 17 is formed from an acrylic plastic. Stand 13 is made of chrome plated steel, and housing 11 is formed of fiberglass. The various threaded screws and rods such as 82A (FIG. 2) are made out of stainless steel while the knurled knobs such as 84A are made of aluminum. The pump bodies, such as 55A, are molded of acrylic resin but ABS plastic, stryene plastic or rigid vinyl would be suitable. Diaphragm 151 is made of soft vinyl, but KRATON TM elastomer or rubber are also suitable. The valves 171 and 173 may be made out of similar materials, although presently KRATON elastomer is used. The pump rods 67B as well as the flanges such as 65 and 63 are made of acrylic resin, although ABS plastic or styrene are also suitable. In the PL/IR pump (FIG. 5) ball valves 185 are made of ethylene propylene while the springs 186 are made of stainless steel. O-rings 181 are made of soft vinyl, KRATON or rubber. Filter 175 is made of cotton or foam plastic. The moving coil 83 can be purchased already fabricate from a source of acoustic speaker parts, such as Quam Nichols, Marquette Rd. and Prairie Ave., Chicago, Ill. 60637. The coil 83 as purchased is mounted on a thin aluminum cylinder; plate 87 is also made of aluminum, and Coil 83 is attached to plate 87 by an epoxy adhesive. Shaft 89 is made of aluminum, while bushing 90 and housing part 94 is made of TEFLON TM polytetrafluoroethylene. Spring 91 and the various screws such 88 are made of stainless steel. Magnet 79 is a ceramic magnet and plates 76A and 76B are made of any permeable steel. Braided wire 95 is a lead wire such as No. P-1603 lead wire available from the Montgomery Company, Canal Bank, Windsor Locks, Conn. 06096.

Turning now to the operation of the system, if the intended use is to be in surgery or other use where sterile or very clean conditions are necessary, all parts of the system that contact the lavage fluid will likely have been removed after the last use, and thus these parts will have to be attached. These parts include the fluid supply bag 15, lines 19, 24A, 24B, 21, 23 and 25, drainage bag 18, couplings 24C and 24D, filter 28, T's 22A and 22B, lavage handpiece 27, and pumps 51A and 51B. All these parts are made out of cheap materials, and all, except perhaps the drainage bag 18, are resterilizable, and thus either a new set of these parts or a set that has been resterilized may be used. The pumps are inserted as shown by the dotted lines in FIG. 3 and the door 74B is closed forcing wedges 75B between fingers 71B causing them to separate and grip flanges 69B and 69B' on pump 51B thereby locking it in place, the door is latched and knob 84A is screwed tight. The distance between flanges 69B and 69B' on pump 51B generally will be made different than the distance between the corresponding flanges 69A and 69A' on pump 51A, with corresponding differences in fingers 71A and 71B, so that a suction pump cannot be inserted in the PL/IR pump chamber and vice versa. All other replaceable parts listed above are attached and the system is primed and checked for leaks prior to surgery or other use. The system is activated by turning switches 31 and 33 to the desired position and knobs 35, 37, 39 and 41 to the desired settings.

When switch 31 is in the lavage position, the adjustment of the pulsations per second knob 37 changes the reciprocation frequency of the motor driving pump 51A. Since the power to the pump has not been changed, the pump stroke will change in order that the net power output of the motor remains the same. This results in the average pressure of the fluid flow and the rate of fluid flow remaining the same, providing the response of amplifier 101 is flat with respect to frequency. In the preferred embodiment the frequency range available is between approximately 7 to 40 cycles per second.

When switch 31 is in the lavage position, the adjustment of knob 35 changes the power amplifier 101 applies to motor 53a. Since the frequency signal does not change (assuming knob 37 is not moved) the motor responds by changing its stroke length. If the power is increased the motor stroke length is increased and if the power is decreased the stroke length is decreased. The change in stroke length changes the amount of fluid pumped in a given stroke and thus changes both the rate of flow and the pressure. The ability of the motor, and thus the reciprocating pump to change its stroke length in response to a change in power provides a much simpler, more reliable and more efficient means of changing the rate of flow or pressure as compared to the prior art. The embodiment described allows the pressure to be varied from about 1 to 75 PSI and flow rates to be adjusted up to about 1300 ml/min. Other ranges of pressure and flow rates of course may be obtained.

When knob 31 is placed in the irrigation mode, the control of PL/IR pump 51A passes to knob 39. The frequency is set by the "behind the set" control to about 40 cycles per second. Control 39 is calibrated so that a maximum flow rate of about 200 ml/min. is obtained. This provides a somewhat finer control of the flow rate than that obtained with control 35. In this mode, the rate of flow and pressure may be varied without concern about the frequency setting. The ability to switch between a lavage and irrigation mode with knob 31 permits a surgeon to set desired lavage settings with knobs 35 and 37, to switch to irrigation mode without changing the settings of knobs 35 and 37, and then return to the pulsatile lavage mode with the settings already set at their desired positions. It is noted that the irrigation mode settings can be duplicated in the lavage mode, and thus a principal advantage of having the separate irrigation function is that it permits rapid switching between a selected "steady" flow setting and a selected "pulsatile" setting.

The aspiration function may be selected by turning knob 33 to suction, and then adjusting knob 41 for the desired suction rate or vacuum pressure. The range of suction available in the preferred embodiment is from about 1 to 300 mm of mercury which corresponds to a maximum air flow rate of about 45 liters per minute. The frequency of the suction motor is fixed by the "behind the set" control 116 to between 10 and 40 cycles per second with 25 cycles per second being the preferred frequency setting.

It is noted that because there will be mixtures of air and liquids in suction line 25, the operation of the suction pump 51B will result in cavitation. The pump 51B has been designed to reduce the noise produced by this cavitation. The flexible diaphragm 151 will absorb a certain amount of shock, and the filter 175 also provides a muffling effect.

The setting of the controls will produce the desired type of lavage stream at nozzle 143B and the desired suction at nozzle 143A. The flow of fluid and the suction provided may be controlled directly at the site by use of pinch valves 133 and 135 on lavage handpiece 141. Generally these valves are used for "off" and "on" functions. Valve 133 has been designed so that it will remain in its closed position until it is pushed forward, and valve 135 has been designed so that it will remain at its closed position until serrated arm 137 is lifted to release an open pinch valve 135. In the preferred embodiment, pinch valve 133 is opened by moving pinch valve 133 away from the body of the lavage handpiece 27, while likewise pinch valve 35 moves away from the body 132 of the handpiece 27 when opened. This enables a simultaneous "spreading" movement of pinch valves 133 and 135 to affect a simultaneous opening of both lines 23 and 25. Likewise, when a cessation of operation is desired, a simple squeezing movement of both valves 133 and 135 can be effected. This "outward-inward" operation of the valves facilitates spontaneous operation of the lavage handpiece 27 as a fluid shut-off and attenuation device to augment the system's control board 29.

After use, the disposable parts mentioned above may be thrown away, or portions of them, such as bag 15 may be thrown away and the other portions resterilized. It is noted that the slow speed at which the linear motors generally operate enables the pumps 51A and 51B to be built without the need for precision tolerances, reinforcing, and/or overly strong materials. This factor contributes to the disposability of the pumps. It is further noted that design of pumps 51A and 51B, the connections to and the supports of the pumps, and the gripping feature activated by the closing of the doors such as 74B enables the pumps to be quickly and easily replaced by persons unskilled in mechanical assembly, with a minimum of directions. In addition, by producing the fluid lines 19, 21, 23, and 25 already connected to the lavage handpiece 27, the fluid supply bag 15 and the pumps 51A and 51B and by having the remaining connections restricted by their physical dimensions, erroneous connections by operating personnel are avoided.

After use, the drainage tank 17 may be replaced with a sterilized tank, or the tank 17 may be used with a disposable bag 18, which is shown in FIG. 2. This bag permits sanitary reuse of the same drainage tank 17 without sterilization, and facilitates laboratory analysis of the drained material.

It is a feature of the invention that each of the steps in the removal and insertion of the pumps can be done preciesly with little skill. The opening of the door releases the pumps without the need for screwdrivers, wrenches, etc. The pumps can be slid out and new pumps can be slid in easily because the fit is loose. At the same time the fit is sure since the fingers, such as 71A, and pin, such as 61, guide the operations which can only be done in one obvious way. Again, no screwdriver or wrenches are needed to secure the pumps as this is done by closing the door and the screwing in of knobs such as 84A. Knob 84A and rod 82A provide the leverage needed for locking the pumps in place. Yet the initial placement of rod 84A in slot 80A is very easy, since both parts are relatively large and are in an open and obvious position. This permits the lavage system of the invention to be utilized by doctors, nurses or other para-medical personnel who may not be skilled with machinery. If there is a breakage of the parts under stress the damage will be contained within the pump housings, such as 68B.

A novel lavage system that provides a sterilizable and disposable fluid system that can be quickly and easily replaced by unskilled persons and has numerous other features and advantages has been disclosed. While the above description of the invention has been referenced to a few particular embodiments, it is evident that, now that the advantages of having lavage system pump parts loosely supported in the replacement mode and the advantages of a door-activated pump chamber gripping system in a lavage system have been disclosed, those skilled in the art can now make numerous uses of, modifications of, and departures from the specific embodiments described herein without departing from the inventive concepts. For example, many different types of pumps may be utilized, including peristaltic type pumps, the coupling and gripping mechanisms may be replaced with many equivalent mechanisms, and the door such as 74A may have many variations, some of which could include covers that are not attached by hinges, provided it performs the closing function. It is also anticipated that other features may be combined with the invention. Consequently, the invention is to be construed as embracing each and every novel feature and novel combination of features within the appended claims.

What I claim is:

1. Medical, dental or therapeutic lavage apparatus comprising:
    a motor having a drive member;
    a pump housing including a door;
    a pump having a pump body and a driven member, said pump body comprising a pump chamber;
    a means for coupling said motor drive member with said driven member for movement in unison in a longitudinal direction; and
    a means activated by the closing of said door for gripping said pump body and securing it within said pump housing to oppose movement of said pump body in the longitudinal direction;
    said means for gripping and securing comprises:
    a pair of gripping members, at least one of said members moveable relative to the other member; and
    a means for forcing said gripping members to engage at least a portion of said pump body in opposing directions.

2. The lavage appartus of claim 1 wherein said at least a portion of said pump body comprises at least one flange and said means for gripping comprises a means for gripping the flange.

3. The lavage apparatus of claim 2 wherein:
    said portion of said pump body comprises a pair of flanges spaced sufficiently apart on said pump body that said gripping members will fit between them and sufficiently close that movement of said gripping members can engage both flanges; and
    said means for forcing comprises a wedge means mounted on said door for forcing said gripping members apart and into contact with said flanges when said door is closed.

4. The lavage apparatus as in claim 3 wherein there are two pairs of said flanges and two pairs of gripping members, each pair of flanges located on opposing sides of said pump body from the other pair.

5. The lavage apparatus of claim 1 wherein said means for gripping and securing includes wedge means mounted on said 6. The lavage apparatus of claim 5 wherein:
    said means for gripping and securing further comprises a pair of fingers, at least one of which is moveable with respect to the other;
    said pump body includes a means for receiving said pair of fingers; and
    said wedge means are spaced on said door to insert between said fingers when said door is closed.

7. The lavage apparatus of claim 5 wherein said means for gripping and securing includes a means for supporting said pump body within said housing, and said wedge means comprises means for locking said pump body to the means for supporting.

* * * * *